United States Patent
Kubo et al.

(10) Patent No.: US 8,586,766 B2
(45) Date of Patent: Nov. 19, 2013

(54) METHOD FOR PRODUCING EPISULFIDE COMPOUND

(75) Inventors: Mineki Kubo, Osaka (JP); Hiroshi Horikoshi, Chiba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/577,298

(22) PCT Filed: Feb. 21, 2011

(86) PCT No.: PCT/JP2011/053649
§ 371 (c)(1),
(2), (4) Date: Aug. 6, 2012

(87) PCT Pub. No.: WO2011/105319
PCT Pub. Date: Sep. 1, 2011

(65) Prior Publication Data
US 2012/0309987 A1 Dec. 6, 2012

(30) Foreign Application Priority Data
Feb. 25, 2010 (JP) .................................. 2010-040407

(51) Int. Cl.
C07D 331/02 (2006.01)
C07D 409/12 (2006.01)
C07D 303/00 (2006.01)

(52) U.S. Cl.
USPC ................ 549/90; 549/59; 549/200; 549/512

(58) Field of Classification Search
USPC ................ 549/29, 59, 90, 200, 512
See application file for complete search history.

(56) References Cited

U.S. PATENT DOCUMENTS

| 5,807,975 | A | 9/1998 | Amagai et al. | |
| 5,945,504 | A | 8/1999 | Amagi et al. | |
| 6,201,061 | B1 * | 3/2001 | Amagai et al. | 524/720 |
| 6,444,146 | B2 * | 9/2002 | Yoshimura et al. | 264/1.32 |
| 6,534,589 | B1 * | 3/2003 | Yoshimura et al. | 524/765 |
| 7,183,441 | B2 * | 2/2007 | Kondo et al. | 568/63 |
| 7,309,794 | B1 * | 12/2007 | Amagai et al. | 549/90 |
| 8,389,671 | B2 * | 3/2013 | Takeuchi et al. | 528/380 |
| 2010/0331515 | A1 | 12/2010 | Takeuchi et al. | |

FOREIGN PATENT DOCUMENTS

| JP | 9-71580 | 3/1997 |
| JP | 9-110979 | 4/1997 |
| JP | 9-255781 | 9/1997 |
| JP | 2000-186087 | 7/2000 |
| JP | 2001-163871 | 6/2001 |
| JP | 2001-163872 | 6/2001 |
| JP | 2001-163874 | 6/2001 |
| JP | 2002-128826 | 5/2002 |
| JP | 2005-232464 | 9/2005 |
| JP | 2006-257421 | 9/2006 |

OTHER PUBLICATIONS

Behzad Zeynizadeh et al., "Solvent-Free Conversion of Epoxides to Thiiranes by Thioures/NH4CI System, Phosphorus, Sulfur and Silicon and the Related Elements", Department of Chemistry, Faculty of Scuebces, Urmia University, Urmia, Iran, Feb. 4, 2008, pp. 2280-2286, vol. 183, No. 9.

Search report from International Application No. PCT/JP2011/053649, mail date is Mar. 29, 2011.

* cited by examiner

Primary Examiner — Golam M M Shameem
(74) Attorney, Agent, or Firm — Greenblum & Bernstein, P.L.C.

(57) ABSTRACT

A problem to be solved by the present invention is to provide an episulfide compound efficiently from an epoxy compound with no need of a measure against odor or corrosion, or a neutralization step. The present invention solved the above-described problem by a method for producing an episulfide compound in which an epoxy compound and a thiourea are reacted with each other in the presence of an ammonium compound.

8 Claims, No Drawings

METHOD FOR PRODUCING EPISULFIDE COMPOUND

TECHNICAL FIELD

The present invention relates to a method for producing an episulfide compound, and specifically to a method for producing an episulfide compound preferable for an optical material such as a plastic lens, a prism, an optical fiber, an information recording substrate, a filter or the like, especially a plastic lens.

BACKGROUND ART

Plastic materials are lightweight, highly tough and easy to be dyed, and therefore are widely used recently for various types of optical materials, especially eyeglass lenses. Optical materials, especially eyeglass lenses, are specifically required to have, as physical properties, low specific gravity, high transparency and low yellow index, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number is decreased. Thus, it has been studied to improve both of the refractive index and the Abbe number. Among methods which have been proposed, a representative method uses an episulfide compound as described in Patent Documents 1 through 3.

However, an episulfide compound found in these patent documents is likely to generate an oligomer or a polymer depending on the reaction conditions, and as a result, the reaction yield is reduced. Therefore, optimization of the reaction conditions for producing an episulfide compound has been desired.

Regarding the reaction conditions for episulfidation, Patent Document 4 proposes a technique of allowing a reaction to proceed in a mixture solvent of a polar organic solvent and a non-polar organic solvent in the presence of an acid and/or an acid anhydride.

Patent Document 5 proposes a method of using only a polar solvent as a reaction solvent, and Patent Document 6 proposes a method of generating an isothiuronium salt as an intermediate substance in the presence of an acid. These methods both result in a low yield and are not practically usable. In addition, these methods require a large amount of acid and also a base for hydrolysis, and therefore require many steps and thus are disadvantageous also in the aspect of cost.

Patent Document 7 proposes a method of forming an epoxy compound into a corresponding isothiuronium salt and then performing hydrolysis thereon by use of ammonia or an ammonium salt. However, this method also requires a large amount of acid for generating the isothiuronium salt and a large amount of ammonia or ammonium salt for performing hydrolysis thereon. This complicates the production process, which is disadvantageous in the aspect of cost. In addition, since there is no description on the yield, it is not clear whether the method is practically usable or not.

As described above, for producing an episulfide compound, methods of adding an acid have been proposed. However, the methods described in these documents have been desired to be improved for the reasons that the acids used in these document mostly accompany a bad odor and thus require a measure against the odor, that the methods require a measure against corrosion, and that the methods may occasionally require a large amount of base for neutralization.

CITATION LIST

Patent Literature

Patent Document 1: Japanese Laid-Open Patent Publication No. Hei 9-71580
Patent Document 2: Japanese Laid-Open Patent Publication No. Hei 9-110979
Patent Document 3: Japanese Laid-Open Patent Publication No. Hei 9-255781
Patent Document 4: Japanese Laid-Open Patent Publication No. 2000-186087
Patent Document 5: Japanese Laid-Open Patent Publication No. 2001-163872
Patent Document 6: Japanese Laid-Open Patent Publication No. 2001-163874
Patent Document 7: Japanese Laid-Open Patent Publication No. 2001-163871

SUMMARY OF INVENTION

Technical Problem

A problem to be solved by the present invention is to provide an episulfide compound efficiently from an epoxy compound with no need of a measure against odor or corrosion, or a neutralization step.

Solution to Problem

As a result of accumulating active studies in light of such circumstances, the present inventors solved the above-described problem by a method for producing an episulfide compound in which an epoxy compound and a thiourea are reacted with each other in the presence of an ammonium compound, and thus achieved the present invention.

Namely, the present invention is as follows.

<1> A method for producing an episulfide compound, wherein an epoxy compound having a structure expressed by the following formula (1) and a thiourea are reacted with each other in the presence of an ammonium salt to produce an episulfide compound having a structure expressed by the following formula (2).

[Chemical formula 1]

(1)

(2)

<2> The method for producing an episulfide compound according to <1> above, wherein the compound of the formula (1) is expressed by the following formula (3), and the compound of the formula (2) is expressed by the following formula (4):

[Chemical formula 2]

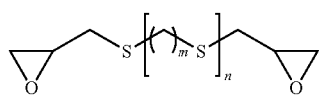
(3)

(where m represents an integer of 0 to 4, and n represents an integer of 0 or 1);

[Chemical formula 3]

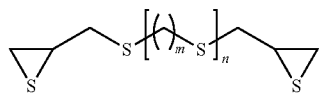
(4)

(where m represents an integer of 0 to 4, and n represents an integer of 0 or 1).

<3> The method for producing an episulfide compound according to <1> or <2> above, wherein the ammonium salt is at least one selected from the group consisting of ammonium nitrate, ammonium sulfate and ammonium chloride.

<4> The method for producing an episulfide compound according to any one of <1> through <3> above, wherein the episulfide compound and the thiourea are reacted with each other with no addition of an acid.

Advantageous Effects of Invention

According to the present invention, it has now become possible to provide an episulfide compound efficiently from an epoxy compound without using a measure against odor or corrosion, or acid required for a neutralization step, which are required in the conventional art.

DESCRIPTION OF EMBODIMENTS

According to the present invention, any of all episulfide compounds having a structure expressed by formula (2) above are usable. Specific examples thereof will be described regarding each type of compounds, i.e., compounds having a chain aliphatic structure, compounds having an aliphatic cyclic structure, and compounds having an aromatic structure.

The compounds having a chain aliphatic structure include compounds expressed by the following formula (4):

[Chemical formula 4]

(4)

(where m represents an integer of 0 to 4, and n represents an integer of 0 or 1).

The compounds having an aliphatic cyclic structure include compounds expressed by the following formula (5) or (6):

[Chemical formula 5]

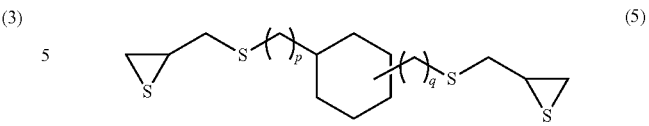
(5)

(where p and q each represent an integer of 0 to 4).

[Chemical formula 6]

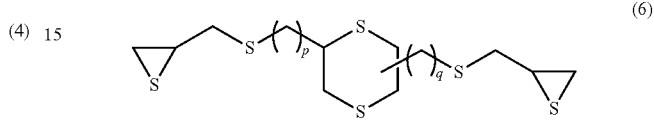
(6)

(where p and q each represent an integer of 0 to 4).

The compounds having an aromatic structure include compounds expressed by the following formula (7):

[Chemical formula 7]

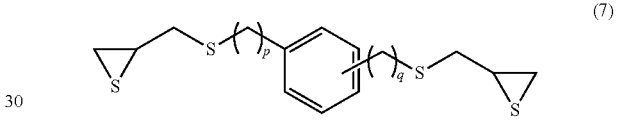
(7)

(where p and q each represent an integer of 0 to 4).

Among the above-shown compounds, the compounds expressed by formula (4) above having a chain aliphatic structure are preferable. Specific examples thereof include bis(β-epithiopropyl)sulfide, bis(β-epithiopropyl)disulfide, bis(β-epithiopropyl)trisulfide, bis(β-epithiopropylthio)methane, 1,2-bis(β-epithiopropylthio)ethane, 1,3-bis(β-epithiopropylthio)propane, 1,4-bis(β-epithiopropylthio)butane, and bis(β-epithiopropylthioethyl)sulfide. Bis(β-epithiopropyl)sulfide (in formula (4), n=0) and bis(β-epithiopropyl)disulfide (in formula (4), m=0, n=1) are especially preferable. Bis(β-epithiopropyl)sulfide (in formula (4), n=0) is most preferable.

Examples of the episulfide compounds having an aliphatic cyclic structure include 1,3- and 1,4-bis(β-epithiopropylthio)cyclohexane (in formula (5), p=0, q=0), 1,3- and 1,4-(β-epithiopropylthiomethyl)cyclohexane (in formula (5), p=1, q=1), bis[4-(β-epithiopropylthio)cyclohexyl]methane, 2,2-bis[4-β-epithiopropylthio)cyclohexyl]propane, bis[4-(β-epithiopropylthio)cyclohexyl]sulfide, 2,5-bis(β-epithiopropylthio)-1,4-dithiane (in formula (6), p=0, q=0), 2,5-bis(β-epithiopropylthiomethyl)-1,4-dithiane (in formula (6), p=1, q=1), 2,5-bis(β-epithiopropylthioethylthiomethyl)-1,4-dithiane, and the like.

Examples of the episulfide compounds having an aromatic structure include 1,3- and 1,4-bis(β-epithiopropylthio)benzene (in formula (7), p=0, q=0), 1,3- and 1,4-bis(β-epithiopropylthiomethyl)benzene (in formula (7), p=1, q=1), bis[4-(β-epithiopropylthio)phenyl)]methane, 2,2-bis[4-(β-epithiopropylthio)phenyl]propane, bis[4-β-epithiopropylthio)phenyl)]sulfide, bis[4-(β-epithiopropylthio)phenyl)]sulfine, 4,4-bis(β-epithiopropylthio)biphenyl, and the like.

An epoxy compound used as a material in the present invention is obtained as a result of substituting sulfur atoms in 3-membered rings in episulfide described above with oxygen atoms.

The amount of thiourea used in the present invention may be any amount which is equal to or greater than the stoichiometric amount. In consideration of economy, the amount of thiourea is usually 1.0 to 5.0 equivalent, preferably 1.0 to 2.0 equivalent, and most preferably 1.1 to 1.8 equivalent.

According to the present invention, any of all ammonium salts is usable. Preferably usable ammonium salts are ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate, and ammonium hydroxide. Ammonium nitrate, ammonium sulfate, and ammonium chloride are more preferable. Ammonium nitrate is most preferable.

The amount of the ammonium salt is usually 0.01 to 20% by weight with respect to the total amount of epoxy in consideration of economy. The amount is preferably 0.1 to 15% by weight, and most preferably 0.5 to 10% by weight. When the amount is less than 0.01% by weight, insoluble substances may be deposited at the time of extraction and washing. When the amount is more than 20% by weight, the number of times of washing required for removing the ammonium salt may be increased, and thus the amount of waste liquid may be increased.

For the reaction of the present invention, a solvent may or may not be used. Usually, a solvent is used. Preferably, a mixture solvent of a non-polar solvent in which the epoxy compound is soluble and a polar solvent in which the thiourea is soluble is used. The volumetric ratio of the polar solvent and the non-polar solvent is usually polar solvent/non-polar solvent=0.1 to 10.0, and preferably 0.2 to 5.0. When the volumetric ratio is less than 0.1, the thiourea is not sufficiently dissolved and thus the reaction does not proceed sufficiently. When the volumetric ratio exceeds 10.0, the reaction proceeds excessively fast and it is difficult to control the reaction.

Examples of a usable non-polar solvent include aliphatic hydrocarbons such as pentane, hexane, heptane and the like; and aromatic hydrocarbons such as benzene, toluene and the like. Aromatic hydrocarbons are preferable, and toluene is most preferable.

Examples of a usable polar solvent include alcohols such as methanol, ethanol and the like; ethers such as diethylether, tetrahydrofuran, dioxane and the like; hydroxyethers such as methylcellosolve, ethylcellosolve, bitylcellosolve and the like; and ketones such as acetone, methylethylketone and the like. Alcohols are preferable, and methanol is most preferable.

Merely a polar solvent may be used. In this case also, the reaction of episulfidation can be caused to proceed by adding an epoxy compound little by little to the polar solvent while taking time.

The reaction is caused by mixing and stirring an epoxy compound, which is a material of the episulfide compound, and an ammonium salt and a reaction solvent used in the present invention. These components may be added in any order, or may be mixed at the same time.

The reaction temperature is usually 0 to 60° C., preferably 10 to 50° C., and most preferably 10 to 40° C. When the reaction temperature is lower than 0° C., the reaction rate is decreased. When the reaction temperature is higher than 60° C., the episulfide compound obtained may be colored. There is no specific limitation on the reaction time as long as the reaction is completed under the above-described conditions. The reaction time is usually 20 hours or less, and preferably 15 hours or less. Regarding the pressure, either reduced pressure, normal pressure or raised pressure may be used. Normal pressure is preferable. The reaction is preferably caused in a nitrogen atmosphere.

After the reaction is finished, the intended episulfide compound is obtained by extraction, washing and removal of the solvent by distillation. As a solvent for extraction, any of the non-polar solvents described above is usable. Aromatic hydrocarbons are preferable, and toluene is most preferable. Washing is performed with water or an aqueous solution of acid. Preferably, washing is first performed with an aqueous solution of acid and then with water. The removal of the solvent by distillation is usually performed at a reduced pressure.

The episulfide compound thus obtained can be refined by a refinement method of recrystallization, reprecipitation, column separation, processing with an adsorber, processing with an ion exchange resin or the like. The production of the episulfide compound can be performed in the air, but is preferably performed in a nitrogen atmosphere in order to guarantee that the components and the resultant compound are not oxidized or colored.

EXAMPLES

Hereinafter, the present invention will be specifically described by way of examples, but the present invention is not limited to the following examples.

Example 1

305 g of thiourea, 1360 ml of methanol, 680 ml of toluene, 10 g of ammonium nitrate, and 146 g of bis(β-epoxypropyl)sulfide (in formula (3), n=0) were mixed and reacted at 20° C. for 9 hours in a nitrogen atmosphere. During the reaction, no polymer was deposited. After the reaction, 1720 ml of toluene and 210 ml of 10% aqueous solution of sulfuric acid were put to the reaction vessel to extract the reaction product.

Then, the extracted product was washed with 130 ml of water four times, and toluene was removed by distillation. As a result, 137 g of bis(β-epithiopropyl)sulfide (in formula (4), n=0) was obtained. The yield was 77%. The results are shown in Table 1.

Examples 2 through 4

The procedure of Example 1 was repeated except that instead of ammonium nitrate, an ammonium salt shown in Table 1 was used in an equal weight amount to that of ammonium nitrate. The results are shown in Table 1.

Example 5

The procedure of Example 1 was repeated except that the amount of ammonium nitrate was 5 g. The results are shown in Table 1.

Comparative Example 1

The procedure of Example 1 was repeated except that ammonium nitrate was not used. During the reaction, polymer was deposited, and bis(β-epithiopropyl)sulfide was not obtained. The results are shown in Table 1.

Comparative Example 2

The procedure of Example 1 was repeated except that 18 g of acetic anhydride was used instead of ammonium nitrate. The results are shown in Table 1.

Comparative Example 3

The procedure of Example 1 was repeated except that 10 g of acetic anhydride was used instead of ammonium nitrate. The results are shown in Table 1.

Comparative Example 4

The procedure of Example 1 was repeated except that 10 g of acetic acid was used instead of ammonium nitrate. The results are shown in Table 1.

Example 6

305 g of thiourea, 3000 ml of methanol, 1500 ml of toluene, 10 g of ammonium nitrate, and 325 g of 1,3-bis(β-epoxypropylthiomethyl)benzene were mixed and reacted at 20° C. for 9 hours in a nitrogen atmosphere. During the reaction, no polymer was deposited. After the reaction, 3800 ml of toluene and 460 ml of 10% aqueous solution of sulfuric acid were put to the reaction vessel to extract the reaction product. Then, the extracted product was washed with 300 ml of water four times, and toluene was removed by distillation. As a result, 288 g of 1,3-bis(β-epithiopropylthiomethyl)benzene (in formula (7), p=1, q=1) was obtained. The yield was 81%. The results are shown in Table 2.

Example 7

The procedure of Example 6 was repeated except that instead of ammonium nitrate, ammonium sulfate was used in an equal weight amount to that of ammonium nitrate. The results are shown in Table 2.

Comparative Example 5

The procedure of Example 6 was repeated except that 18 g of acetic anhydride was used instead of ammonium nitrate. The results are shown in Table 2.

TABLE 1

| Example | Added compound | Amount (g) | Odor | Yield (%) |
|---|---|---|---|---|
| Example 1 | Ammonium nitrate | 10 | No | 77 |
| Example 2 | Ammonium sulfate | 10 | No | 76 |
| Example 3 | Ammonium chloride | 10 | No | 76 |
| Example 4 | Ammonium acetate | 10 | No | 75 |
| Example 5 | Ammonium nitrate | 5 | No | 76 |
| Comparative example 1 | None | — | No | 0 |
| Comparative example 2 | Acetic anhydride | 18 | Yes | 75 |
| Comparative example 3 | Acetic anhydride | 10 | Yes | 71 |
| Comparative example 4 | Acetic acid | 10 | Yes | 66 |

TABLE 2

| Example | Added compound | Amount (g) | Odor | Yield (%) |
|---|---|---|---|---|
| Example 6 | Ammonium nitrate | 10 | No | 81 |
| Example 7 | Ammonium sulfate | 10 | No | 80 |
| Comparative example 5 | Acetic anhydride | 18 | Yes | 62 |

Example 8

305 g of thiourea, 3000 ml of methanol, 1500 ml of toluene, 10 g of ammonium nitrate, and 332 g of 1,4-bis(β-epoxypropylthiomethyl)cyclohexane were mixed and reacted at 20° C. for 9 hours in a nitrogen atmosphere. During the reaction, no polymer was deposited. After the reaction, 3800 ml of toluene and 460 ml of 10% aqueous solution of sulfuric acid were put to the reaction vessel to extract the reaction product. Then, the extracted product was washed with 300 ml of water four times, and toluene was removed by distillation. As a result, 295 g of 1,4-bis(β-epithiopropylthiomethyl)cyclohexane (in formula (5), p=1, q=1) was obtained. The yield was 80%. The results are shown in Table 3.

Example 9

The procedure of Example 8 was repeated except that instead of ammonium nitrate, ammonium sulfate was used in an equal weight amount to that of ammonium nitrate. The results are shown in Table 3.

Comparative Example 6

The procedure of Example 8 was repeated except that 18 g of acetic anhydride was used instead of ammonium nitrate. The results are shown in Table 3.

TABLE 3

| Example | Added compound | Amount (g) | Odor | Yield (%) |
|---|---|---|---|---|
| Example 8 | Ammonium nitrate | 10 | No | 80 |
| Example 9 | Ammonium sulfate | 10 | No | 79 |
| Comparative example 6 | Acetic anhydride | 18 | Yes | 64 |

Example 10

305 g of thiourea, 3000 ml of methanol, 1500 ml of toluene, 10 g of ammonium nitrate, and 373 g of 2,5-bis(β-epoxypropylthiomethyl)-1,4-dithiane were mixed and reacted at 20° C. for 9 hours in a nitrogen atmosphere. During the reaction, no polymer was deposited. After the reaction, 3800 ml of toluene and 460 ml of 10% aqueous solution of sulfuric acid were put to the reaction vessel to extract the reaction product. Then, the extracted product was washed with 300 ml of water four times, and toluene was removed by distillation. As a result, 340 g of 2,5-bis(β-epithiopropylthiomethyl)-1,4-dithiane (in formula (6), p=1, q=1) was obtained. The yield was 83%. The results are shown in Table 4.

Example 11

The procedure of Example 10 was repeated except that instead of ammonium nitrate, ammonium sulfate was used in an equal weight amount to that of ammonium nitrate. The results are shown in Table 4.

Comparative Example 7

The procedure of Example 10 was repeated except that 18 g of acetic anhydride was used instead of ammonium nitrate. The results are shown in Table 4.

TABLE 4

| Example | Added compound | Amount (g) | Odor | Yield (%) |
|---|---|---|---|---|
| Example 10 | Ammonium nitrate | 10 | No | 83 |
| Example 11 | Ammonium sulfate | 10 | No | 81 |
| Comparative example 7 | Acetic anhydride | 18 | Yes | 64 |

As described above, in Examples 1 through 7, an epoxy compound and a thiourea were reacted with each other in the presence of an ammonium salt, and as a result, an episulfide compound was obtained at a high yield of 75% or higher. In addition, in each of the examples which do not require an acid, unlike in the comparative examples, generation of odor was prevented, and neither a measure against corrosion or a neutralization step is necessary. Therefore, the present invention can produce an episulfide compound efficiently and can also improve the work environment and simplify the production process.

The invention claimed is:

1. A method for producing an episulfide compound, wherein an epoxy compound having a structure expressed by the following formula (1) and a thiourea are reacted with each other in the presence of an ammonium salt to produce an episulfide compound having a structure expressed by the following formula (2):

[Chemical formula 1]

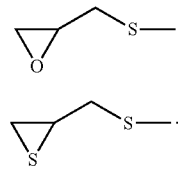

(1)

(2)

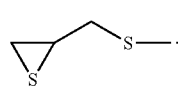

2. The method for producing an episulfide compound according to claim 1, wherein the compound of the formula (1) is expressed by the following formula (3), and the compound of the formula (2) is expressed by the following formula (4):

[Chemical formula 2]

(3)

(where m represents an integer of 0 to 4, and n represents an integer of 0 or 1);

[Chemical formula 3]

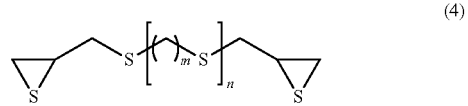

(4)

(where m represents an integer of 0 to 4, and n represents an integer of 0 or 1).

3. The method for producing an episulfide compound according to claim 1, wherein the ammonium salt is at least one selected from the group consisting of ammonium nitrate, ammonium sulfate and ammonium chloride.

4. The method for producing an episulfide compound according to claim 1, wherein the episulfide compound and the thiourea are reacted with each other with no addition of an acid.

5. The method for producing an episulfide compound according to claim 2, wherein the ammonium salt is at least one selected from the group consisting of ammonium nitrate, ammonium sulfate and ammonium chloride.

6. The method for producing an episulfide compound according to claim 2, wherein the episulfide compound and the thiourea are reacted with each other with no addition of an acid.

7. The method for producing an episulfide compound according to claim 3, wherein the episulfide compound and the thiourea are reacted with each other with no addition of an acid.

8. The method for producing an episulfide compound according to claim 5, wherein the episulfide compound and the thiourea are reacted with each other with no addition of an acid.

* * * * *

UNITED STATES PATENT AND TRADEMARK OFFICE
CERTIFICATE OF CORRECTION

PATENT NO. : 8,586,766 B2  
APPLICATION NO. : 13/577298  
DATED : November 19, 2013  
INVENTOR(S) : M. Kubo et al.

Page 1 of 1

It is certified that error appears in the above-identified patent and that said Letters Patent is hereby corrected as shown below:

On Title Page, (56) References Cited, U.S. Patent Documents of the printed patent, change "5,945,504 A 8/1999 Amagi et al" to -- 5,945,504 A 8/1999 Amagai et al --.

Signed and Sealed this  
Fifteenth Day of July, 2014

Michelle K. Lee  
*Deputy Director of the United States Patent and Trademark Office*